United States Patent
Collins et al.

(10) Patent No.: US 8,146,402 B2
(45) Date of Patent: Apr. 3, 2012

(54) DYNAMIC COEFFICIENT OF FRICTION MEASURING DEVICE HAVING A TRACK WITH AN ARCUATE PORTION

(75) Inventors: Mark Collins, Sussex (GB); David Robert Bunting, Hertfordshire (GB)

(73) Assignee: Surface Control Limited, Middlesex (GB)

( * ) Notice: Subject to any disclaimer, the term of this patent is extended or adjusted under 35 U.S.C. 154(b) by 448 days.

(21) Appl. No.: 12/443,126

(22) PCT Filed: Sep. 26, 2007

(86) PCT No.: PCT/GB2007/003675
§ 371 (c)(1),
(2), (4) Date: Mar. 26, 2009

(87) PCT Pub. No.: WO2008/038001
PCT Pub. Date: Apr. 3, 2008

(65) Prior Publication Data
US 2009/0320556 A1   Dec. 31, 2009

(30) Foreign Application Priority Data

Sep. 26, 2006 (GB) .................................. 0618935.1
May 30, 2007 (GB) .................................. 0710316.1

(51) Int. Cl.
*G01N 19/02* (2006.01)
(52) U.S. Cl. ............................................................ 73/9
(58) Field of Classification Search .................. None
See application file for complete search history.

(56) References Cited

U.S. PATENT DOCUMENTS 3,828,605 A    8/1974  Fazekas
4,081,989 A    4/1978  Majcherczyk
(Continued)

FOREIGN PATENT DOCUMENTS

AU    560 050 B2    3/1987
(Continued)

OTHER PUBLICATIONS

Keith R Andrew et al: "Measurement of energy loss profiles during short duration sliding contacts: a computer-compatible instrument based on the British Pendulum Skid Tester" Measurement Science and Technology, Institute of Physics Publishing, Bristol, GB, vol. 9, No. 9, Sep. 1, 1998, pp. 1566-1570, XP020064599 ISSN: 0957-0233.*

(Continued)

*Primary Examiner* — Harshad Patel
(74) *Attorney, Agent, or Firm* — Heslin Rothenberg Farley & Mesiti P.C.

(57) ABSTRACT

The invention provides a device for measuring the dynamic coefficient of friction of a surface. The device includes a track having an arcuate portion which is shaped to mimic an arc of travel of a pendulum; a shoe mounted so as to be movable along the track, and a biasing device for biasing part of the shoe into contact with the surface as it moves along the arcuate portion of the track; a propulsion device for providing an initial propulsion force to propel the shoe along the track; a velocity detector for measuring the velocity of the shoe at a plurality of points during its travel along the track; and computing device for calculating the coefficient of friction from changes in velocity of the shoe as it moves along the track.

12 Claims, 9 Drawing Sheets

U.S. PATENT DOCUMENTS

| | | | |
|---|---|---|---|
| 4,594,878 A * | 6/1986 | Abe et al. | 73/9 |
| 4,672,838 A * | 6/1987 | Reh | 73/9 |
| 4,722,218 A | 2/1988 | Strader | |
| 4,813,266 A | 3/1989 | Nash | |
| 4,895,015 A | 1/1990 | English | |
| 5,195,357 A | 3/1993 | Takino et al. | |
| 5,259,236 A | 11/1993 | English | |
| 5,736,630 A | 4/1998 | Welner | |
| 2006/0277973 A1 * | 12/2006 | Bailey | 73/9 |

FOREIGN PATENT DOCUMENTS

| | | |
|---|---|---|
| FR | 2751748 A1 | 1/1998 |
| SU | 473937 | 6/1975 |
| WO | WO2008038001 A2 | 4/2008 |
| WO | WO2008038001 A3 | 4/2008 |

OTHER PUBLICATIONS

International Search Report for PCT/GB2007/003675 dated Nov. 30, 2007.

Written Opinion of the International Searching Authority for PCT/GB2007/003675 dated Apr. 7, 2008.

Andrew, Keith R. et al., Measurement of energy loss profiles during short duration sliding contacts: a computer-compatible instrument based on the British Pendulum Skid Tester, Measurement Science and Technology, vol. 9 (Sep. 1, 1998), pp. 1566-1570.

http://www.attar.com.au/slipt.html, Advanced Technology Testing and Research, Slip Resistance Testing, Feb. 5, 2001.

http://www.attar.com.au/Slip_resistance, Advanced Technology Testing and Research, Slip Resistance Testing, Aug. 20, 2006.

UK Patent Office Search Report dated Aug. 16, 2007 for UK patent application No. 0710316.1.

* cited by examiner

DYNAMIC COEFFICIENT OF FRICTION MEASURING DEVICE HAVING A TRACK WITH AN ARCUATE PORTION

CROSS REFERENCE TO RELATED APPLICATIONS

This application is a §371 national stage filing of PCT International Application No. PCT/GB2007/003675 filed on Sep. 26, 2007 and published in English on Apr. 3, 2008 as PCT publication WO 2008/038001 A2, which claims the benefit of priority from British application number GB 0618935.1, filed on Sep. 26, 2006, and British application number GB 0710316.1, filed on May 30, 2007. The entire disclosures of these applications are incorporated herein by reference.

FIELD OF THE INVENTION

This invention relates to a device for determining the slip resistance of a surface, more particularly, the invention relates to a device for determining the slip resistance of a floor surface.

BACKGROUND OF THE INVENTION

According to the UK Health & Safety Executive's own statistics, slips, trips and falls on level ground consistently count for around 1 in 3 major injuries, and for over 1 in 5 injuries in workplace areas throughout Great Britain that result in a 3 day absence from work. The HSE statistics indicate that there are at least 35,000 injuries per annum due to slips, trips and falls and suggest that the majority of these accidents are slips.

Various factors contribute to slipping accidents, and the HSE have identified six factors considered to be of particular importance:
  The nature of the floor
  Contamination of the floor
  Footwear considerations
  Pedestrian factors
  Cleaning
  Environment The Workplace, (Health, Safety and Welfare) Regulations, 1992, require that floors must not be slippery, so as to expose any person to a risk to their safety. Methods have been developed for testing the inherent slipperiness of a floor surface, and two methods of measuring the slipperiness of a floor are referred to in HSE publications. These are the 'pendulum Coefficient of Friction (CoF) test; and a surface micro-roughness meter test.

The pendulum coefficient of friction test is now the subject of a British Standard, BS 7976. The pendulum test instrument (TRL Pendulum Tester) uses an arm with a rubber shoe mounted on the end that swings from a fixed height. The contact arc chord length and depth are carefully controlled. The shoe is raised vertically against a spring that controls the pressure on the floor. Frictional engagement with the floor results in a loss of momentum and consequently so the swinging arm rises to a lower height at the end of the swing. A scale converts the reduced height into a coefficient of friction measurement.

Although the pendulum instrument is considered to provide an accurate assessment of the slipperiness of a floor in both dry and contaminated (e.g. wet conditions), it suffers from the drawback that it requires a skilled operative both to use it and to interpret the results. Moreover, according to the HSE, the pendulum meter is currently the only portable instrument that accurately simulates the action of a foot slipping on a wet floor.

The slipperiness of a floor may also be gauged by measuring the surface roughness of a flooring material. A number of types of roughness tests exist (see the HSE publication: 'The assessment of pedestrian slip risk' published by the Health and Safety Executive 10/04) and such methods, in theory, give a good indicator of floor slip resistance.

The surface micro-roughness meters measure a parameter known as the 'Rz' parameter which is calculated as the mean value of several peak-to valley measurements on the floor surface. According to the HSE, in most circumstances, both pendulum CoF and surface micro-roughness readings are required to give an accurate indicator of the slipperiness of a floor surface. The HSE classification of slip risk, based on pendulum measurements, classifies pendulum values of 0-24 as high risk, values of 25-35 as moderate risk, values of 36-64 as low risk and values of 65+ as extremely low risk.

The classification for Rz surface roughness (microns) states that a surface roughness of below 10 microns is classified as providing a high potential for slip, a surface roughness between 10 and 20 microns is classified as providing a moderate potential for slip, whereas a surface roughness of 20 or above is stated to provide a low potential for slip.

A major problem with the methods and instruments currently available for measuring the slipperiness of a floor is that, in practice, they require near laboratory conditions, and require setting up and data interpretation by skilled personnel. They are therefore not suitable for routine use and regular floor monitoring in an average work environment such as a supermarket where the condition of the floor, and hence its slipperiness, will typically fluctuate considerably, i.e. through changes in the type and extent of contamination of the floor, alteration of the floor substrate, changes in the cleaning personnel, change in the staff using the test equipment and poor statistical record monitoring. Therefore, at present, there remains a need for an apparatus that is simple to set up and use and which can be used by unskilled staff, i.e. staff that have little or no knowledge or understanding of slip causes or staff with only a minimum of training, to determine whether or not a floor is safe for the public to walk over.

SUMMARY OF THE INVENTION

The present invention sets out to provide an apparatus for monitoring the condition of a floor that is quick and simple to set up and use and can be used by staff with a minimum of training.

The invention provides a device for measuring the dynamic coefficient of friction of a surface, the device comprising;
  a track having an arcuate portion which is shaped to mimic an arc of travel of a pendulum;
  a shoe mounted so as to be movable along the track, and means for biasing part of the shoe into contact with the surface as it moves along the arcuate portion of the track;
  means for providing an initial propulsion force to propel the shoe along the track;
  means for measuring the velocity of the shoe at a plurality of points during its travel along the track; and
  computing means for calculating the coefficient of friction from changes in velocity of the shoe as it moves along the track.

The shoe is mounted so as to be movable along the track. It may, for example, be mounted on a carriage that is slidably mounted on the track The arcuate track is shaped to mimic an arc of travel of a pendulum, i.e. the track is bowed in a downwards direction. The arcuate track can be formed by a rail or pair of substantially parallel rails upon which is mounted a carriage that carries the shoe. The carriage may be provided with one or more rollers or pairs of rollers that engage the track and allow the carriage to move along the track. The arcuate track may have a substantially horizontal portion of track adjoining one or both ends thereof The device comprises means for providing an initial propulsion force to propel the shoe along the track. The means for providing the initial propulsion force is typically configured so that it imparts an accelerating force to the shoe (or carriage carrying the shoe) up to but not beyond the start of the arcuate portion of the track. Once the accelerating force is removed, the shoe (or carriage) will gradually lose velocity as it moves along the arcuate portion of the track as a consequence of frictional engagement with the underlying surface. The velocity of the shoe (or carriage) is measured by a plurality (e.g. two or more, for example three or more, and in particular three) of measuring devices and the reduction in velocity is determined. Since the rate of deceleration of the shoe is dependent on the friction between the shoe and the underlying surface, the rate of deceleration can be used to calculate the dynamic coefficient of friction of the surface.

The measuring devices can comprise electromagnetic radiation sensors and associated electromagnetic radiation emitters. For example, each measuring device can comprise a device for emitting and forming a beam of infra red or ultraviolet radiation or visible light and a sensor to detect the said beam. The emitting device and sensor are positioned so that the beam is directed across the track. Movement of the shoe or carriage carrying the shoe is then detected by virtue of the shoe or carriage passing through and breaking the beam. At least two emitter/sensor couples are disposed along the track and the time taken for the shoe or carriage to break each successive beam provides a means of measuring the velocity of the shoe or carriage as it moves along the track.

The means for providing an initial propulsion force can take a number of different forms. For example, it could be a solenoid-driven or hydraulic ram or plunger. Preferably, however, it comprises a spring which is compressed and then released.

In one preferred embodiment, the means for providing an initial propulsion force comprises a compressible spring, a mechanism for compressing the spring, a latch for holding the spring in a compressed state, and release means for releasing the latch to allow the spring to decompress.

In order to ensure that part of the shoe remains in contact with the surface as it travels along the arcuate portion of the track, a biasing means is provided for biasing the shoe against the surface. The biasing means typically takes the form of a biasing spring.

The part of the shoe that is biased into contact with the surface may be formed from any one of a variety of materials such as rubber or leather. More typically, the shoe is formed of rubber, and most preferably a 4S grade of rubber as defined herein.

The device may be calibrated using a pendulum tester, e.g. a TRL pendulum tester, in which case the arcuate portion of the track has a radius of curvature corresponding to the radius of the path followed by the pendulum in the pendulum tester. Calibration may be achieved using the methods described below.

In another aspect, the invention provides a method of measuring the dynamic coefficient of friction of a surface using a device as described in herein; wherein the method comprises;

positioning the device on the surface;

imparting an initial propulsion force to the shoe to propel the shoe along the track;

measuring the velocity of the shoe at a plurality of points during its travel along the track; and calculating the coefficient of friction from changes in velocity of the shoe as it moves along the track.

The device may form part of an apparatus for determining the slip resistance of a floor surface at a plurality of locations on the floor surface, wherein the apparatus comprises:

a location device for identifying and recording a location of the apparatus;

a device for measuring the dynamic coefficient of friction of the surface as hereinbefore defined;

means for measuring one or more further physical properties of the floor surface relevant to slip resistance at each location;

a data processor programmed to compare measured values for each of the said physical properties of the floor surface at each location with comparison data; and an output device operatively linked to the data processor for informing a user of the apparatus whether the slip resistance of the floor at a given location is within acceptable limits.

Thus, the apparatus of the invention may comprise means for measuring two or more physical properties of the floor surface relevant to slip resistance at each location, one of the said physical properties being the dynamic coefficient of friction of the surface, and the other one or more other physical properties being selected from:

a) the micro-profile of the floor surface, and b) the reflectance of the surface.

In one embodiment, the apparatus comprises: (i) a device for measuring the dynamic coefficient of friction of the floor surface as hereinbefore defined; (ii) means for measuring the micro-profile of the floor surface; and (iii) optionally means for measuring the reflectance of the surface.

In a further embodiment, the apparatus comprises:—(i) a device for measuring the dynamic coefficient of friction of the floor surface as hereinbefore defined; (ii) means for measuring the reflectance of the surface; (iii) optionally means for measuring the micro-profile of the floor surface.

In a preferred embodiment, the apparatus comprises:—(i) a device for measuring the dynamic coefficient of friction of the floor surface as hereinbefore defined; (ii) means for measuring the reflectance of the surface; (iii) means for measuring the micro-profile of the floor surface.

The micro-profile of the floor surface can be measured by means of a micron profile meter. Diamond stylus micron profile meters are commercially available and comprise a diamond tipped stylus (e.g. a 2 µm diamond stylus) that is in physical contact with the surface and tracks along the along the surface recording micro-undulations of the surface.

As an alternative to the diamond stylus profile meter, an optical (and hence non-contact) method can be employed in which the peaks and troughs of the surface are detected by scanning a light along the surface for a predetermined distance.

The reflectance of the surface may be measured using a gloss meter. Gloss meters are available commercially and operate by directing light of a predetermined strength onto the surface, and measuring the amount of light reflected back from the surface.

The data processor is programmed to compare measured values for each of the physical properties of the floor surface at each location with comparison data which can, for example, comprise historical data consisting of previously measured values for each location or/and as a reference standard when setting up the first inspection.

The location device is preferably one which is capable of determining the position of the apparatus to an accuracy of within about 5 metres, more preferably within about 4 metres, for example within about 3 metres, and most preferably within about 2 metres. The location device may be provided with a transceiver, and the location of the device may be determined by communication with one or more external transceivers positioned at fixed, known locations relative to the apparatus. For example, where the apparatus is intended for use in a supermarket or department store or other shop, a plurality of transceivers may be positioned at fixed location around the supermarket, store or shop, communication between the external transceivers and the transceiver in the location device serving to establish the location of the apparatus.

Whereas the various component parts of the apparatus can be spatially separated (e.g. the data processor and/or the output device could be remote devices communicating by, for example, radio waves, to the location device and measuring means), it is preferred that the means for measuring one or more physical properties of the floor surface, data processor, output device, and location device (other than any external transceivers) when present, are all mounted in or on a common housing.

The apparatus may have only one output device, or may have a plurality of output devices.

Each output device is operatively linked to the data processor and informs a user of the apparatus whether the slip resistance of the floor at a given location is within acceptable limits. Information regarding the slip resistance can be imparted to the user in a variety of ways. For example, the output device can comprise one or more visual or audio elements for indicating whether the slip resistance of the floor at a given location is within acceptable limits.

In one embodiment, an output device is provided which comprises one or more lights that light up to indicate whether the slip resistance of the floor at a given location is within acceptable limits.

Slip Risk Classification

| | |
|---|---|
| 0-24 | High |
| 25-35 | Moderate |
| 36-64 | Low |
| 65+ | Extremely low |

The lights may comprise green and red indicator lights, the green light indicating that the slip resistance of the floor at a given location is within acceptable limits and the red light indicating that the slip resistance of the floor at a given location is not within acceptable limits.

Alternatively or additionally, an output device may be present which provides an alphanumeric visual display. The alphanumeric visual display can be provided by, for example, a screen or a printer or both.

In one preferred embodiment, an output device is present which provides a print out informing the user of the slip resistance of the floor.

The output devices typically provide information which informs the user whether or not the floor meets a predetermined slip resistance requirement without the requirement for the user to carry out complex calculations and without the need for any particular skill or experience on the part of the user. For example, the output device may provide an index number or letter indicative of the state of the floor so that the user can see, either straightaway or by reference to a simple key or chart, whether the floor requires attention. In one embodiment, the output device may also provide information as to what type of remedial action is required. It will be appreciated therefore that the apparatus may be used by an unskilled or semi-skilled operative.

In another aspect, the invention provides an apparatus for determining the slip resistance of a floor surface at a plurality of locations on the floor surface, the apparatus comprising:
  a device for measuring the dynamic coefficient of friction of a surface as hereinbefore defined;
  means for measuring one or more further physical properties of the floor surface relevant to slip resistance at each location;
  a data processor programmed to compare measured values for each of the said physical properties of the floor surface at each location with comparison data; and
  an output device operatively linked to the data processor for informing a user of the apparatus whether the slip resistance of the floor at a given location is within acceptable limits.

The apparatus preferably comprises a location device as hereinbefore defined for identifying and recording the location of the apparatus.

In a still further aspect, the invention provides a method of monitoring the slip resistance of a floor surface at one or more locations on the floor surface, which method comprises using an apparatus as hereinbefore defined to:
(a) measure the dynamic coefficient of friction of a surface and one or more other physical properties of the floor surface relevant to slip resistance at each location;
(b) compare measured values for each of the said physical properties of the floor surface at each location with comparison data; and
(c) inform a user of the apparatus whether the slip resistance of the floor at a given location is within acceptable limits.

Further aspects and embodiments of the invention are as set out below and as defined in the claims.

DETAILED DESCRIPTION OF THE INVENTION

The invention will now be illustrated, but not limited, by reference to the specific embodiment shown in the accompanying drawings.

Figure 1:
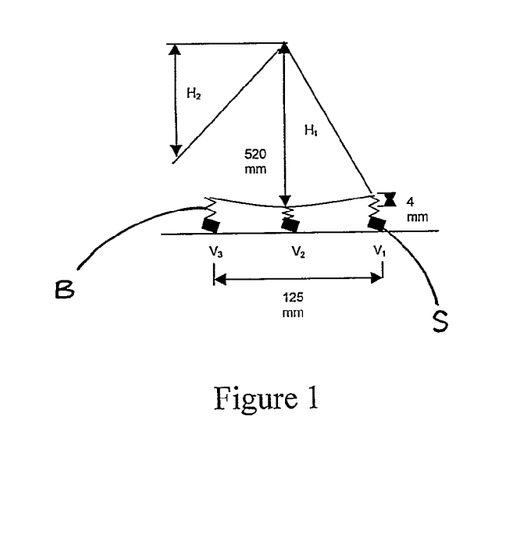
FIG. 1 is a schematic diagram illustrating the mode of action of a conventional pendulum apparatus for measuring the coefficient of friction of a floor surface. The pendulum apparatus does not form part of the invention.

The TRL Pendulum Tester method, which represents the currently approved method of measuring the Coefficient of Friction of floor surfaces, is illustrated schematically in FIG. 1. The pendulum tester uses a swinging pendulum arm with a rubber shoe S mounted on its end. The rubber shoe is formed from 4S rubber ("standard simulated shoe sole"), a grade of rubber developed by the UK Health and Safety Laboratory (HSL) and the UK Slip Resistance Group (UKSRG). The contact arc chord length and depth are carefully controlled using adjustment screws (not shown) on the base of the pendulum tester. As shown in FIG. 1, a typical chord length used in the test is a length of 125 mm. The rubber shoe S is raised vertically against a spring B that controls the pressure on the floor. The pendulum is released from a defined starting height so that it swings down bringing the shoe S into contact with the floor surface. Friction between the shoe S and the floor results in a loss of momentum and so the swinging arm rises to a lower height at the end of the swing. A scale converts this reduced height into a coefficient of friction measurement.

An apparatus according to the invention is shown in FIGS. 2 to 9C. The apparatus provides a more compact and portable alternative to the standard TRL pendulum tester. The apparatus of the invention replicates the behaviour of the pendulum by using a compressed spring G to provide the equivalent potential energy of the pendulum when raised to its starting position.

Figure 2:
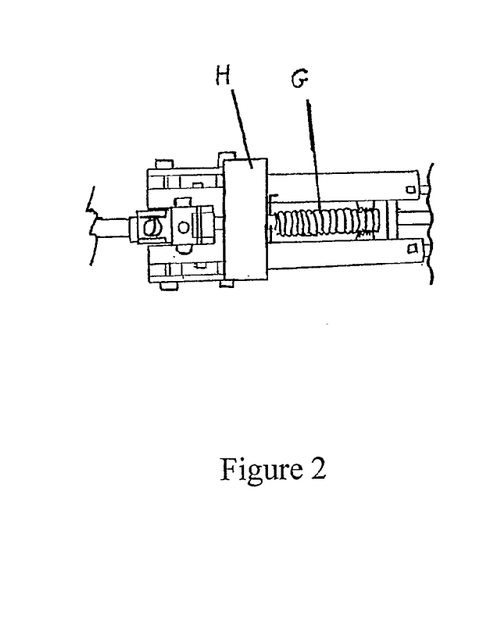
FIG. 2 is a schematic partial view from below of an apparatus for measuring the coefficient of friction of an underlying surface according to one embodiment of the invention.
Figure 3:
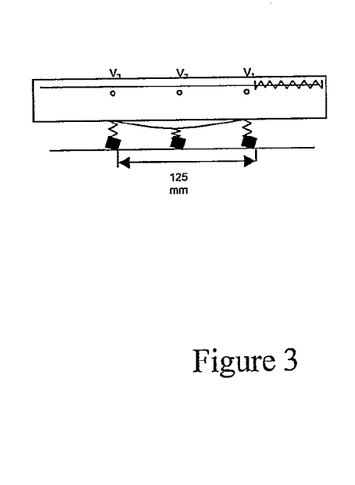
FIG. 3 is a schematic side view of the apparatus of FIG. 2.

As shown schematically in FIGS. 2 and 3, when the force of the compressed spring G is released, it urges a carriage bearing a rubber shoe H along a track I with the same shape as the swing of the pendulum over the distance where the shoe is in contact with the floor. Frictional forces on the shoe slow it down as it passes over the floor surface. The apparatus measures the speed of the shoe at multiple points ($V_1$, $V_2$ & $V_3$) during its travel and from these measurements computes the equivalent pendulum measurement and hence the coefficient of friction of the surface under test.

The following is a simplified description of the measurement equations that neglects a number of effects for simplicity. The potential energy (PE) of the pendulum device is given by $$PE = m \cdot g \cdot h_1$$

where m is the mass in kilograms
g is the acceleration due to gravity, approximately 9.81 $m \cdot s^{-2}$
$h_1$ is the initial height in metres The potential energy is converted to kinetic energy (KE) that is maximum at the lowest point of travel.

$$KE_1 = \frac{1}{2} \cdot m \cdot v_1^2$$

The effect of friction reduces the Kinetic Energy so that the pendulum rises to a lower height at the end of its swing. The potential energy at this point is $$PE_2 = m \cdot g \cdot h_2$$

The height $h_2$ is effectively measured by the pointer on the pendulum that records the maximum height reached.

If the pendulum were released from the height $h_2$, this would result in a Kinetic Energy $$KE_2 = \frac{1}{2} \cdot m \cdot v_2^2$$

The difference between the initial height and the final height is primarily due to the loss of energy to friction. We can set the equations equal $$PE_1 = KE_1 \text{ and } PE_2 = KE_2$$

But we can calculate the loss of Potential Energy as $PE_1 - PE_2$ and therefore $$PE_1 - PE_2 = KE_1 - KE_2$$

The coefficient of friction indicated by the pendulum device can be simply measured as a function (F) of the height difference $h_1 - h_2$, this being indicated on the scale of the machine. The function F is a easily calculated from the geometry of the pendulum machine based on the angle of deflection of the machine's pointer.

So the Coefficient of Friction, $COF = F(h_1 - h_2)$

By transposing the equations above and removing common terms we get $$2 g(h_1 - h_2) = v_1^2 - v_2^2$$

and therefore $$COF = F((v_1^2 - v_2^2)/2 g)$$

It can therefore be seen that by measuring the changes in velocity and relating that difference to the calibration data measured from the pendulum the coefficient of friction can be determined to give the same result as would have been given by the pendulum for the same surface.

Figure 4:
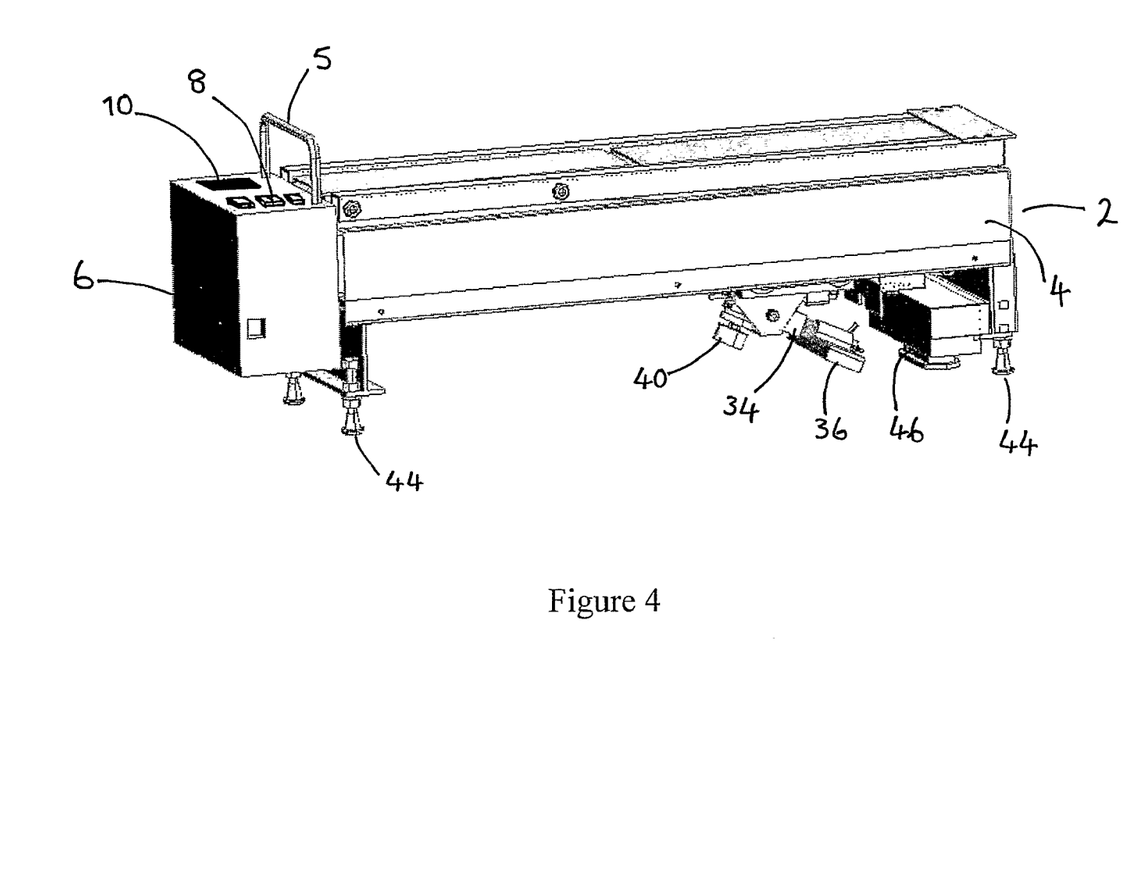
FIG. 4 is an isometric view of an apparatus according to another embodiment of the invention.

An apparatus embodying the principles set out above is illustrated in FIGS. 4 to 9C. As shown in FIG. 4, the apparatus comprises a housing 2 with removable side panels 4 that conceal the moving parts of the apparatus.

Mounted on one end of the support frame is a box 6 that contains a data processor (not shown) and the electronic controls (not shown) for the apparatus. Set into the upper surface of the box are control buttons 8 and a small display screen 10. A handle 5 is secured to the top of the box 6.

The data processor is linked to or contains a memory or data storage device which may be of standard type. For example, the data storage may be provide by a combination of semiconductor RAM, ROM and erasable programmable read-only memory (EPROM), the EPROM memory serving to preserve the data in the absence of power. The processor is linked to a power supply and on/off switch, a number of output devices, a location device, the device for measuring the dynamic coefficient of friction of the underlying floor surface, a gloss meter 46 and optionally a micron profile meter (not shown). The processor is also connected to a USB port (not shown) or other data port so that data can be taken from or introduced into the data processor.

The interior workings of the apparatus are shown in FIGS. 5, 6, 7 and 8 which are side sectional elevations.

Figure 5:
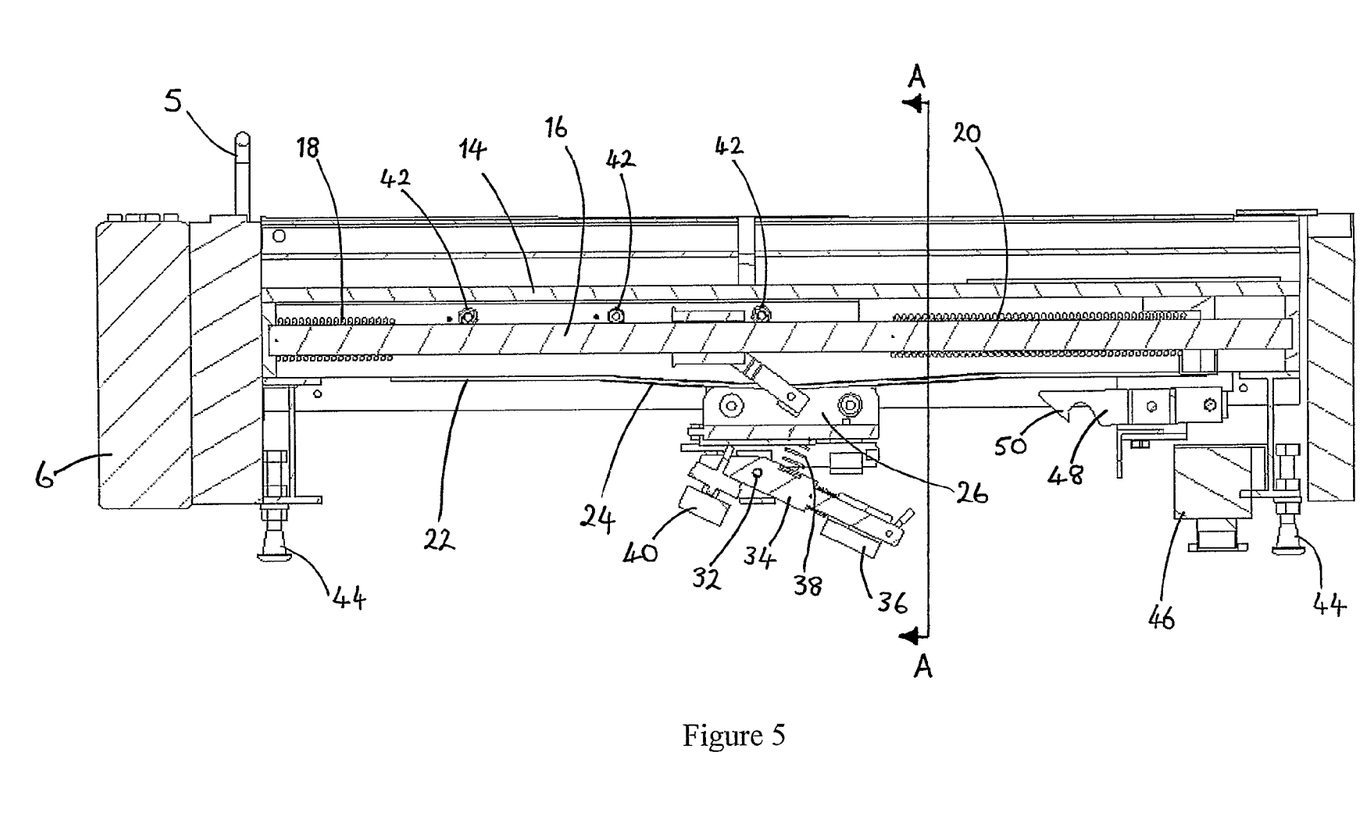
FIG. 5 is a side sectional elevation of the apparatus of FIG. 4 showing a shoe-supporting carriage in mid movement along the track.
Figure 5A:
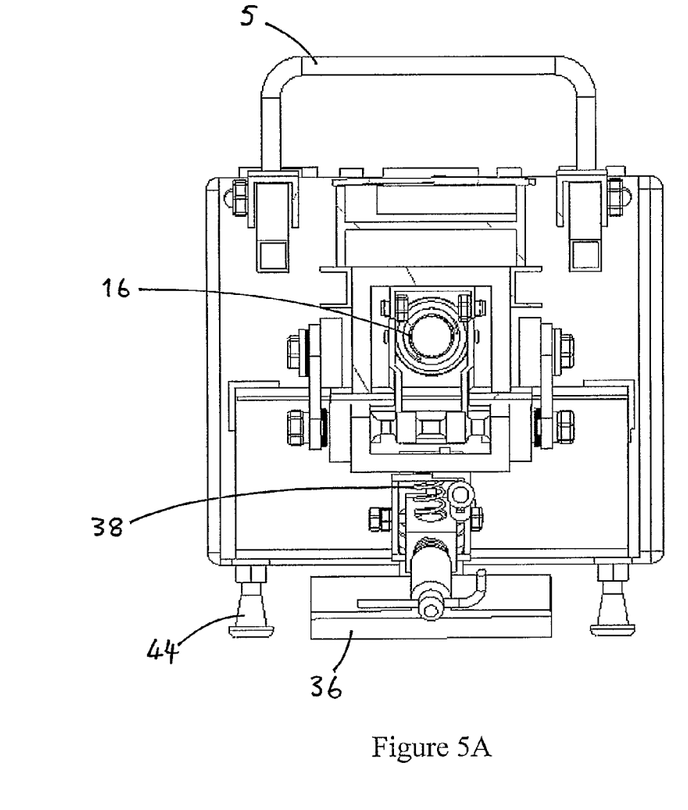
FIG. 5A is a sectional elevation along line A-A in FIG. 5.

Within the housing 2 is a longitudinally extending frame member 14 having an inverted channel section, within which is disposed a bar 16 of circular cross section. A buffering spring 18 is mounted about the bar at one end thereof, and a propulsion spring 20 is mounted about the bar at the other end thereof. The frame member 14 is provided at its lower end with a laterally extending flange 22, which is substantially horizontal at either end but has a central portion 24, which is arcuate in shape. The flange 22 serves as a track upon which is mounted a carriage 26. Two pairs of rollers 28 and 30 serve to hold the carriage in place on the flange.

Attached by means of pivot mounting 32 to the lower part of the carriage is an arm 34, upon which is mounted a shoe 36. The arm 34 and hence the shoe 36 are biased in a downwards direction by means of biasing spring 38. An adjustment screw 40 allows for fine adjustment of the position of the arm 34 and shoe 36.

The shoe may be made from a variety of materials such as rubber and leather. In one preferred embodiment, however, the shoe is formed from the 4S grade or rubber described above.

The housing 2 is provided with adjustable feet, 44, which allow the housing, and hence the shoe 36, to be raised and lowered.

After manufacture and typically before dispatching to a customer or end user, the apparatus is set up by calibrating with a pendulum tester, e.g. a standard pendulum tester. Thus, the adjustment screw 40 and adjustable feet 44 are adjusted so that the set-up corresponds to the set-up of the pendulum tester. After calibration, the adjustable feet 44 are typically locked against further adjustment before the device is sent out to the customer or end user.

Mounted just above the bar 16 are three infrared sensors 42, each consisting of a pair of elements, one of which is an infrared emitting LED and the other of which is an infrared optical transistor. In practice, an infrared beam is established between the LED and transistor, the beam being broken as the carriage is moved along the track. The time taken for the carriage to break each successive beam provides a means of measuring the velocity of the carriage as it moves along the track, and data from the three infrared sensors are conveyed to the controller in the box 6.

As an alternative to using infrared sensors and emitters, other electromagnetic radiation sensors and emitters could be used, for example UV or visible light emitters and sensors.

Located at one end of the housing is a gloss meter, 46, the output from which is conveyed to the data processor within box 6.

Figures 6, 6A:
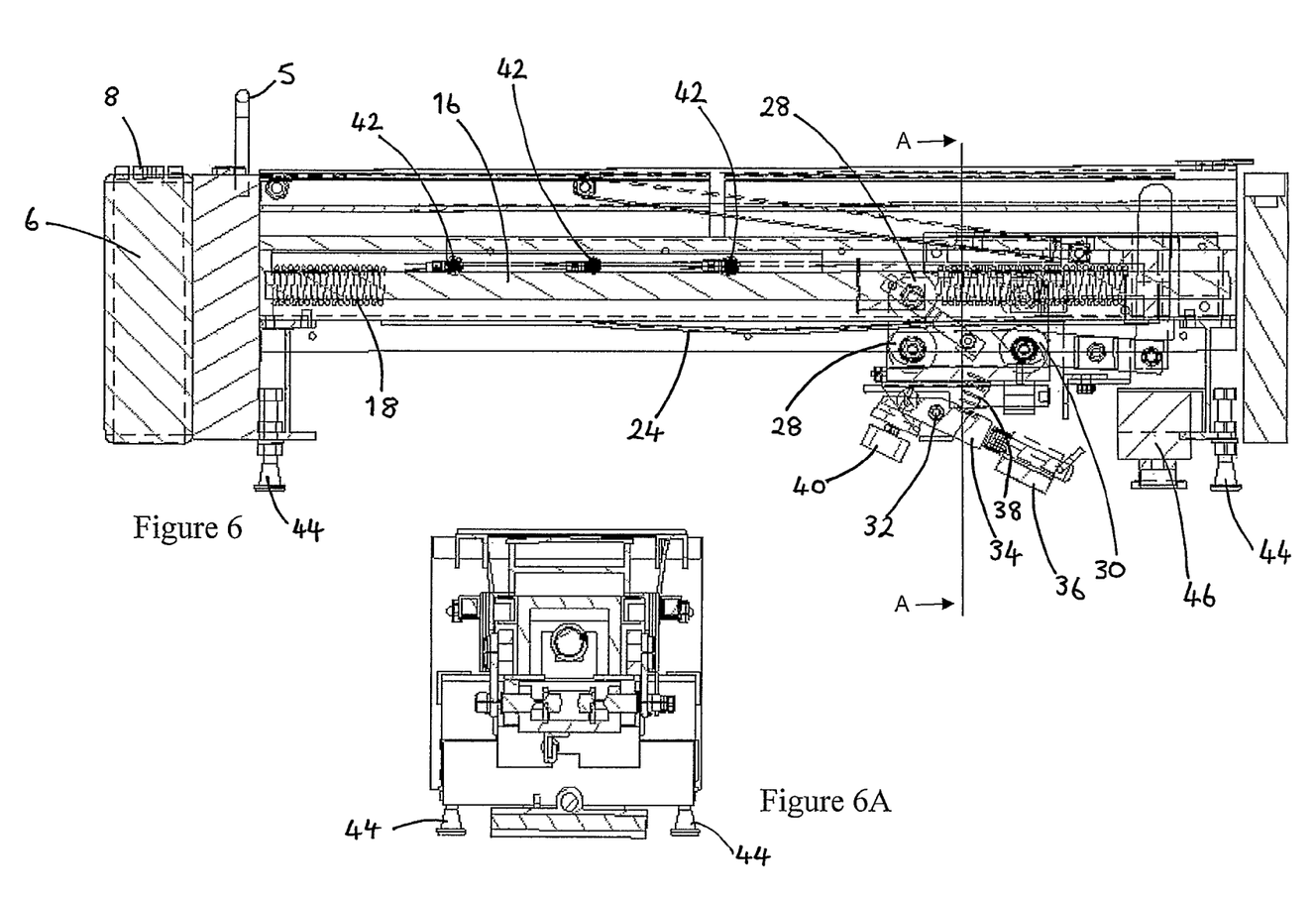
FIG. 6 is a side sectional elevation of the apparatus shown in FIG. 5 with the carriage in the latched primed position.
FIG. 6A is a sectional elevation along line A-A in FIG. 6.

FIG. 6 illustrates the apparatus in a 'loaded' configuration, with the spring 20 in a compressed state. The spring is retained in the compressed state by virtue of the carriage, which is held in place by latch 48. Latch 48 has a hooked latch portion 50 which engages a boss (not shown) on the carriage. A push rod 52 provides a means of releasing the latch.

Figure 8:
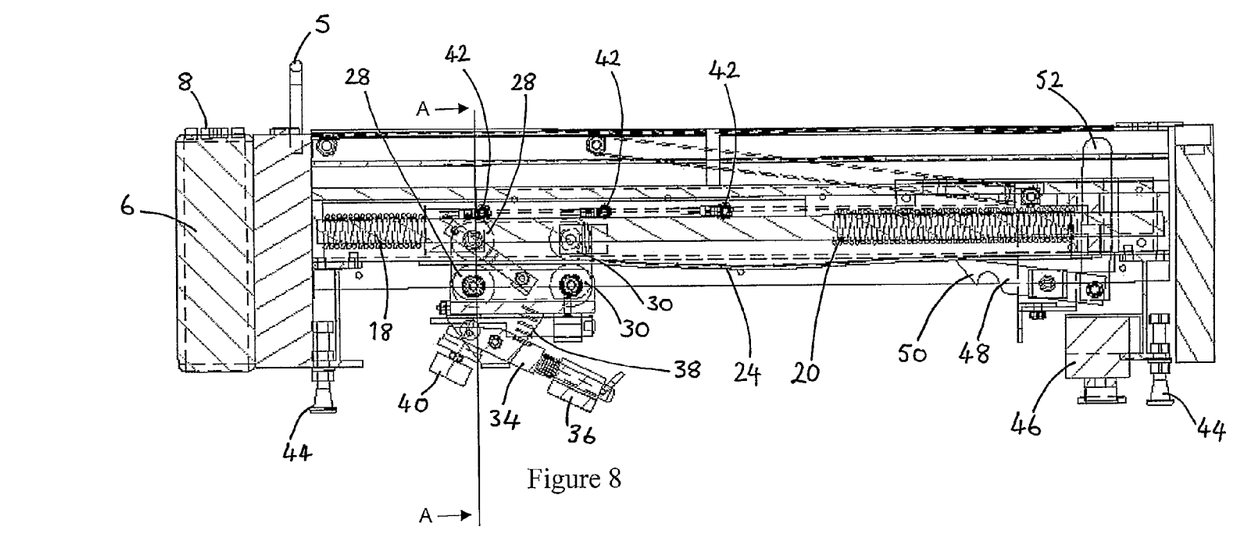
FIG. 8 is a side sectional elevation of the apparatus shown in FIG. 5 showing the carriage at the end of its travel following release of the latch.
Figure 8A:
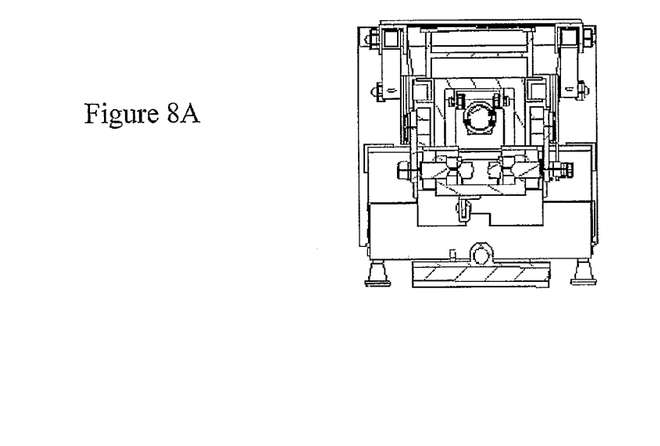
FIG. 8A is a sectional elevation along line A-A in FIG. 8.

FIG. 8 illustrates the apparatus after the push rod 52 has been depressed to release the force of the spring 20 to propel the carriage 26 along the track 22/24.

Figure 9A:
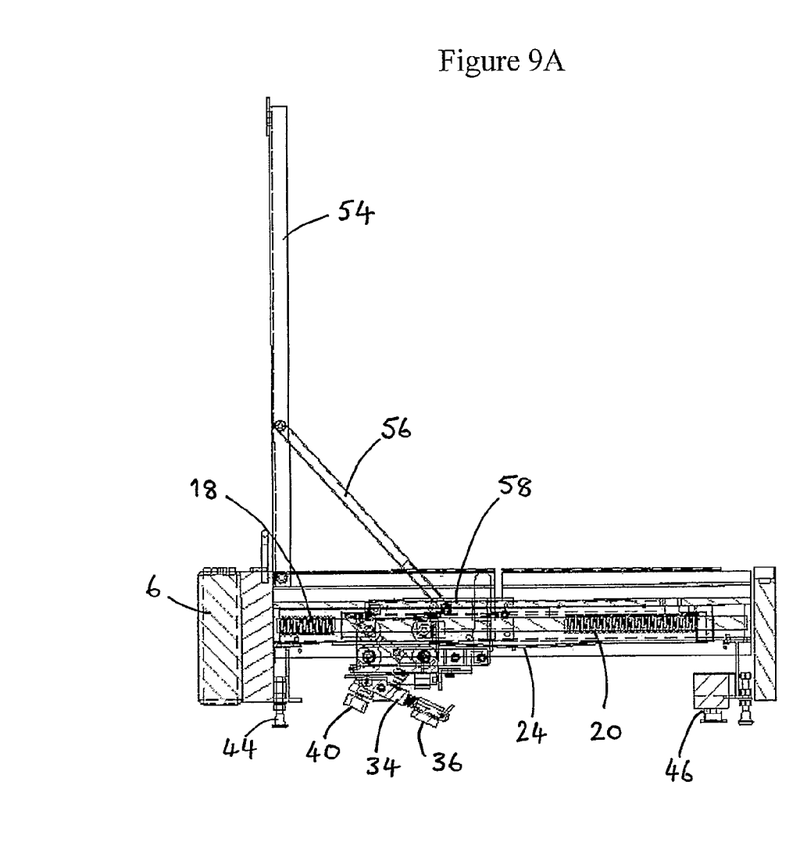
FIG. 9A is a side sectional elevation of the apparatus shown in FIG. 5 with the lever arm in a raised position.
Figure 9B:
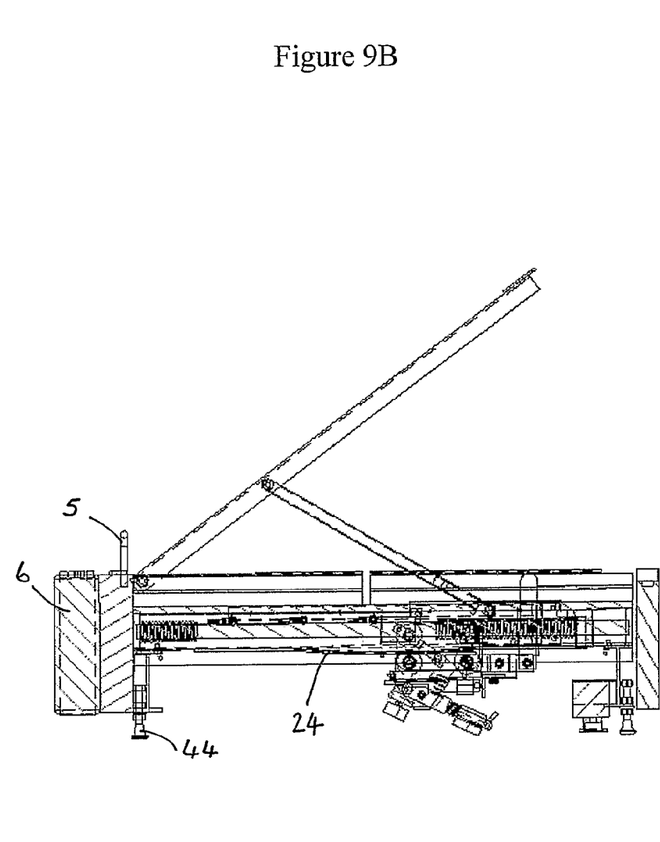
FIG. 9B is a side sectional elevation of the apparatus shown in FIG. 5 with the lever arm in a partially lowered position and the compression spring lightly compressed.
Figure 9C:
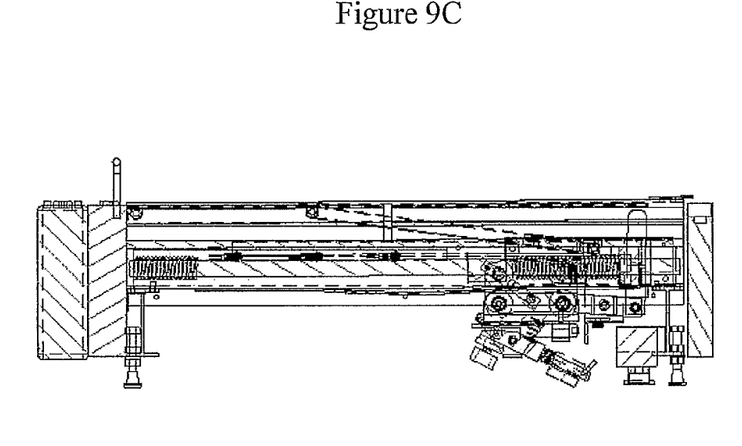
FIG. 9C is a side sectional elevation of the apparatus shown in FIG. 5 with the lever arm in a fully lowered position and the compression spring fully compressed.

FIGS. 9A, 9B, and 9C illustrate the manner in which the propulsion spring 20 is compressed.

Firstly, lever arm 54 is lifted and this has the effect of moving the pivoting strut 56 and an associated slider 58 rearwardly, so that the slider engages the carriage 26. The lever arm is then pivoted towards the closed position as shown in FIG. 9B, moving the slider 58 and carriage 26 into contact with the spring 20, thereby compressing the spring. When the lever arm 54 is fully depressed and is in the fully closed state, the spring is fully compressed and the carriage is held in place by means of the latch 48.

Figure 7:
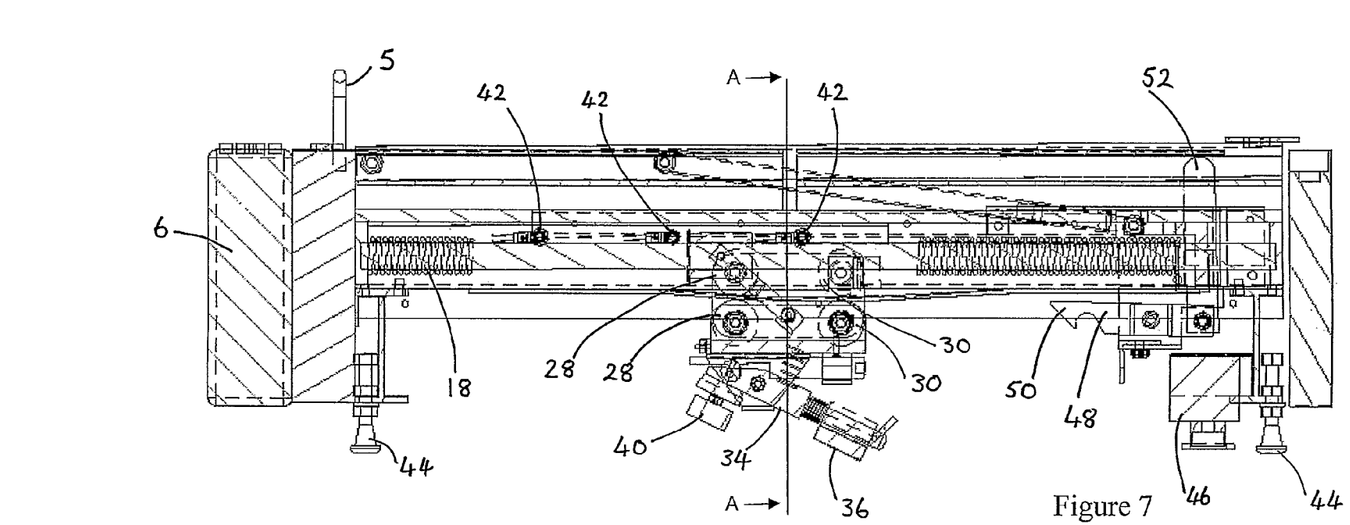
FIG. 7 is a side sectional elevation of the apparatus shown in FIG. 5 showing the position of the carriage shortly after release of the latch.
Figure 7A:
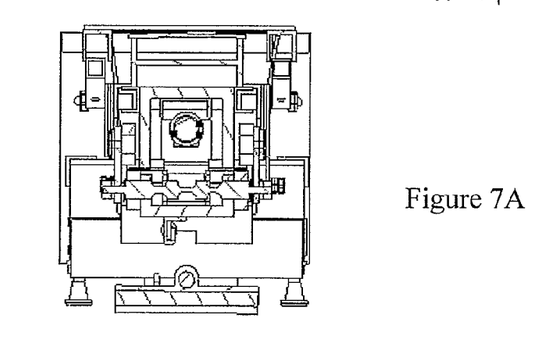
FIG. 7A is a sectional elevation along line A-A in FIG. 7.

In order to use the apparatus, the push rod 52 is depressed thereby lifting the latch member 48 to release the carriage, which is then propelled along the track 22/24. As the carriage moves along the arcuate portion 24 of the track, the shoe 36 comes into contact with the surface, so that friction between the surface and the shoe has the effect of slowing down the movement of the carriage. The rate of deceleration of the carriage is measured by means of the infrared sensors 42. At the end of the track 22, the carriage is brought to a halt by means of the buffering spring 18.

The rate of deceleration of the carriage is a function of the dynamic coefficient of friction of the surface. Computer software in the data processor within the box is capable of converting the measured rates of deceleration of the carriage into coefficient of friction figures. The figures are then either transmitted to a remote device for reading out or are displayed on the display screen 10 on top of the box 6.

The coefficient of friction figures may be combined with readings from the gloss meter 46, to give an easily understood indication of the slip resistance of the floor.

The gloss meter 46 operates by directing a beam of light of a known strength onto the floor surface and then measuring the light reflected back from the floor. The results of the measurements are then relayed to the data processor.

The apparatus may also comprise a micron profile meter ("surface micro-roughness meter") (not shown) which measures the "peak-to-valley" distances of undulations in the floor surface at a number of points within a defined distance and then calculates the mean "peak-to-valley" distance. The measurement can be made using a 2 μm diamond-tipped stylus that follows the profile of the floor surface over a length of, for example, 12 mm, or the measurement can be made by an optical scanning method that involves measuring the peaks and valleys along a 12 mm linear path. An advantage of using the optical scanning method over the diamond tipped stylus method is that it does not involve contact with the floor and hence avoids the potential problem of the stylus becoming clogged or snagged on the surface. Whichever method is used, the micron profile meter conveys to the data processor information about the roughness of the surface.

Thus, the data processor receives measurements from the device for measuring the dynamic coefficient of friction, the gloss meter 46 and, when present, a micron profile meter. The results from each instrument are then compared with reference data. Depending on whether or not the results fall within predefined limits, a simple pass-fail message may be displayed on the display screen 10. Alternatively or additionally, a signal may be sent to an output device on the box which comprises red and green lights, red to indicate that the floor has failed the slip test, and green to indicate that the floor has passed the slip test.

In a further alternative, a signal can also be sent to a second output on the box which comprises a printer (not shown) that can provide a print out of the measured parameters of the floor surface so that the reasons why the floor may have failed the slip test may be determined. A full set of data corresponding to the measurements made can be taken from the apparatus via a USB port (not shown) on the box.

A comparison of data obtained from a particular surface area can be compared with historical data for that area. The historical data can be held in the data storage facility within the apparatus or held at a remote location, e.g. a remote computer. Data can be conveyed to the remote location by cable, or wirelessly or by transfer using a suitable using a suitable data carrier. By comparing the current and historical data for a given area, the deterioration of the surface can be monitored thereby allowing it to be remedied before it reaches a hazardous state.

The advantage of the apparatus of the invention is that it allows the slipperiness of a floor surface to be measured quickly and simply by staff who have received only a minimum of training. For example, after a spillage in a supermarket, the floor may be mopped clean but there may still be traces of residue that could increase the slipperiness of a floor.

Using the apparatus of the invention, the floor can be tested to see whether it is safe to allow members of the public to walk over it. In another example, the apparatus can be used routinely at daily, weekly or even at several times daily intervals to monitor the condition of the floor on an ongoing basis so that problems of floor deterioration and wear can be addressed before they reach a point at which the floor is hazardous.

An advantage of the apparatus shown in FIGS. 2 to 9C is its compact nature. The device is of lightweight construction and is portable in contrast to the more cumbersome pendulum tester devices. The apparatus can be easily carried under one arm and provide a simplified digital read-out indicative of the state of the surface.

EQUIVALENTS

It will readily be apparent that numerous modifications and alterations may be made to the specific embodiments of the invention described above without departing from the principles underlying the invention. All such modifications and alterations are intended to be embraced by this application.

Whatever arrangement is utilised for determining the COF of a floor surface, it will be appreciated that the results obtained will be such that a direct comparison may be deduced in relation to measurements made using the pendulum test instrument in accordance with BS 7976.

The invention claimed is:

1. A device for measuring the dynamic coefficient of friction of a surface, the device comprising;
    a track having an arcuate portion which is shaped to mimic an arc of travel of a pendulum;
    a shoe mounted so as to be movable along the track, and means for biasing a part of the shoe into contact with a surface as it moves along the arcuate portion of the track;
    means for providing an initial propulsion force to propel the shoe along the track;
    means for measuring a velocity of the shoe at a plurality of points during the shoe's travel along the track; and
    computing means for calculating a coefficient of friction from changes in velocity of the shoe as the shoe moves along the track.

2. A device according to claim 1, wherein the means for providing an initial propulsion force comprises a compressed spring.

3. A device according to claim 2, wherein the means for providing an initial propulsion force comprises a compressible spring, a mechanism for compressing the spring, a latch for holding the spring in a compressed state, and release means for releasing the latch to allow the spring to decompress.

4. A device according to claim 1, wherein the part of the shoe is biased into contact with the surface during the shoe's travel along the arcuate portion of the track by means of a biasing spring.

5. A device according to claim 1, wherein the part of the shoe that is biased into contact with the surface is formed of rubber.

6. A device according to claim 1, wherein the means for measuring the velocity comprises means for measuring the velocity of the shoe at three or more positions along the track.

7. A device according to claim 6, wherein the means for measuring the velocity comprises means for measuring the velocity of the shoe at three positions along the track.

8. A device according to claim 1, wherein the arcuate portion of the track is formed by one of a rail and a pair of substantially parallel rails upon which is mounted a carriage that carries the shoe.

9. A device according to claim 8, wherein the carriage is provided with one or more rollers or pairs of rollers that engage the track and allow the carriage to move along the track.

10. A device according to claim 1, wherein the arcuate portion of the track has a substantially horizontal portion of track adjoining one or both ends thereof.

11. A device according to claim 1, wherein the means for measuring the velocity of the shoe comprises electromagnetic radiation sensors and associated electromagnetic radiation emitters.

12. A method of measuring the dynamic coefficient of friction of a surface using a device as described in claim 1, wherein the method comprises:
    positioning the device on the surface;
    imparting an initial propulsion force to the shoe to propel the shoe along the track;
    measuring the velocity of the shoe at a plurality of points during the shoe's travel along the track; and
    calculating a coefficient of friction from changes in velocity of the shoe as the shoe moves along the track.

* * * * *